United States Patent
Kim et al.

(10) Patent No.: US 7,592,488 B2
(45) Date of Patent: Sep. 22, 2009

(54) METHOD FOR PREPARING OPTICALLY ACTIVE AMINES

(75) Inventors: Mahn-Joo Kim, Pohang (KR); Jaiwook Park, Pohang (KR); Won-Hee Kim, Daejeon (KR); Kiwon Han, Paju-shi (KR); Yoon Kyung Choi, Gyeongsangbuk-do (KR)

(73) Assignee: Postech Academy-Industry Foundation, Pohang (KR)

( * ) Notice: Subject to any disclaimer, the term of this patent is extended or adjusted under 35 U.S.C. 154(b) by 35 days.

(21) Appl. No.: 11/840,935

(22) Filed: Aug. 18, 2007

(65) Prior Publication Data

US 2009/0035830 A1  Feb. 5, 2009

(30) Foreign Application Priority Data

Aug. 2, 2007 (KR) ................ 10-2007-0077733

(51) Int. Cl.
*C07C 209/62* (2006.01)
*C07C 209/88* (2006.01)

(52) U.S. Cl. .............. 564/424; 564/413; 564/414; 564/415; 564/437; 549/404

(58) Field of Classification Search ........ None
See application file for complete search history.

(56) References Cited

FOREIGN PATENT DOCUMENTS

| EP | 1036189 | 9/2000 |
|----|---------|--------|
| WO | WO 2006/032776 | 3/2006 |

OTHER PUBLICATIONS

Chem. Eur. J. (2007), 13, p. 2034-2043.*
Chem. Commun., (2005), p. 5307-5309.*
J. Am. Chem. Soc., (2005), 127(50), p. 17620-17621.*
Database CAPLUS on STN, Acc. No. 2005:984386, Akutagawa et al., European Journal of Inorganic Chemistry (2005), 16, p. 3271-3276 (CAPLUS abstract).*
Kim, Mahn-Joo; "Dynamic Kinetic Resolution of Primary Amines with a Recyclable Pd Nanocatalyst for Racemization," *Org. Lett.*, 9:1157-1159 (2007).

* cited by examiner

*Primary Examiner*—Brian J Davis
(74) *Attorney, Agent, or Firm*—Marshall, Gerstein & Borun LLP

(57) ABSTRACT

The present invention relates to a method of preparing optically active amines and chiral amines prepared thereby. The method includes reacting an amine compound, a metal catalyst, a biocatalyst including a lipase, and an acyl donor compound in an organic solvent to obtain a chiral amide compound, and then hydrolyzing the chiral amide compound to obtain a chiral amine.

12 Claims, No Drawings

METHOD FOR PREPARING OPTICALLY ACTIVE AMINES

CROSS-REFERENCE TO RELATED APPLICATION

This application claims priority to and the benefit of Korean Patent Application No. 10-2007-0077733 filed in the Korean Intellectual Property Office on Aug. 2, 2007, the entire contents of which are incorporated herein by reference.

BACKGROUND OF THE INVENTION a) Field of the Invention

The present invention relates to a method of preparing optically active amines and chiral amines prepared thereby. More particularly, the present invention relates to a method of easily preparing optically active chiral amines with high yield and purity, and chiral amines prepared thereby.

b) Description of the Related Art

In general, a method of preparing optically active chiral amines can be categorized into a chemical method using a metal catalyst and a biochemical method using enzymes as a biocatalyst. Recently, a new method of preparing chiral amines including a mixed catalyst of a metal catalyst and a biocatalyst has been researched, but there have been reported only three cases until now. The first case among these was disclosed by a German research team (Reetz, M. T; Schimossek, K. Chimia, 1996, 50, 668) and then by a British research team (Parvulescu, A.; Vos, D. D.; Jacobs, P. Chem. Commun. 2005, 5307). According to them, chiral amines can be synthesized by using a palladium metal catalyst supported on a sulfur oxide of an alkaline-earth metal as a racemization catalyst and lipase as a selective acylation catalyst in a dynamic kinetic resolution method. Another case was disclosed by a Swedish research team (Paetzold, J.; Backvall, J. E. J. Am. Chem. Soc. 2005, 127, 17620). According to the disclosure, chiral amines are synthesized by using a ruthenium metal complex as a racemization catalyst in a dynamic kinetic resolution method. However, these methods have some disadvantages of having a low synthesis yield, using only benzylamine-based materials as a substrate, and having difficulty in reusing a used catalyst.

SUMMARY OF THE INVENTION

One embodiment of the present invention provides a method of easily preparing optically active chiral amines with high yield and purity in a short time.

Another embodiment of the present invention provides chiral amines prepared using the above method.

According to an embodiment of the present invention, provided is a method of preparing a chiral amine that includes: reacting an amine compound represented by the following Formula 1, a metal catalyst, a biocatalyst including a lipase, and an acyl donor compound represented by the following Formula 2 in an organic solvent to obtain a chiral amide compound represented by the following Formula 3; and hydrolyzing the chiral amide compound to obtain a chiral amine represented by the following Formula 4.

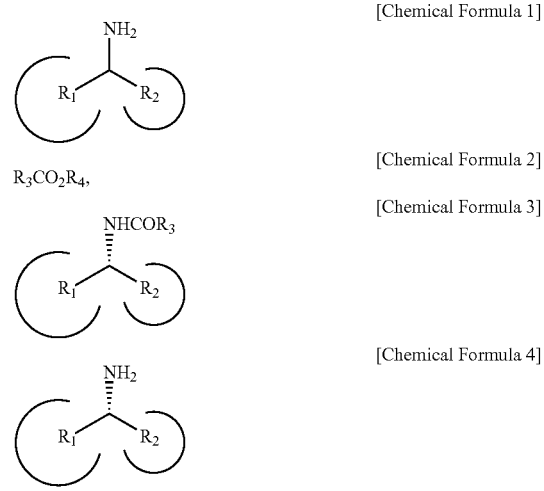

[Chemical Formula 1]

[Chemical Formula 2]

[Chemical Formula 3]

[Chemical Formula 4]

Wherein, in the above Formulae 1 to 4, $R_1$ and $R_2$ are connected to each other to form a ring, or are independently selected from the group consisting of hydroxyl, nitro, amino, azido, amidino, cyano, isocyano, cyanato, thiocyanato, hydrazino, hydrazono, carbonyl, carbamyl, thiocarbamyl, thiol, mesyl, a substituted or unsubstituted ester, carboxyl, or a salt thereof, sulfonic acid or a salt thereof, phosphoric acid or a salt thereof, a substituted or unsubstituted $C_1$-$C_{15}$ alkyl, a substituted or unsubstituted $C_2$-$C_{16}$ alkenyl, a substituted or unsubstituted $C_2$-$C_{16}$ alkynyl, a substituted or unsubstituted $C_6$-$C_{18}$ aryl, a substituted or unsubstituted $C_7$-$C_{18}$ arylalkyl, a substituted or unsubstituted $C_1$-$C_{20}$ heteroalkyl, a substituted or unsubstituted $C_2$-$C_{20}$ heterocycle, a substituted or unsubstituted $C_3$-$C_{20}$ heteroarylalkyl, a substituted or unsubstituted $C_3$-$C_{15}$ cycloalkyl, a substituted or unsubstituted $C_3$-$C_{15}$ cycloalkenyl, a substituted or unsubstituted $C_6$-$C_{15}$ cycloalkynyl, a substituted or unsubstituted $C_3$-$C_{20}$ heterocycloalkyl, and combinations thereof, wherein $R_1$ has a bigger steric size than $R_2$, $R_3$ and $R_4$ are independently selected from the group consisting of hydroxyl, nitro, amino, azido, amidino, cyano, isocyano, cyanato, thiocyanato, hydrazino, hydrazono, carbonyl, carbamyl, thiocarbamyl, thiol, mesyl, a substituted or unsubstituted ester, carboxyl, or a salt thereof, sulfonic acid or a salt thereof, phosphoric acid or a salt thereof, a substituted or unsubstituted C-$C_{15}$ alkyl, a substituted or unsubstituted $C_2$-$C_{16}$ alkenyl, a substituted or unsubstituted $C_2$-$C_{16}$ alkynyl, a substituted or unsubstituted $C_6$-$C_{18}$ aryl, a substituted or unsubstituted $C_7$-$C_{18}$ arylalkyl, a substituted or unsubstituted $C_1$-$C_{20}$ heteroalkyl, a substituted or unsubstituted $C_2$-$C_{20}$ heterocycle, a substituted or unsubstituted $C_3$-$C_{20}$ heteroarylalkyl, a substituted or unsubstituted $C_3$-$C_{15}$ cycloalkyl, a substituted or unsubstituted $C_3$-$C_{15}$ cycloalkenyl, a substituted or unsubstituted $C_6$-$C_{15}$ cycloalkynyl, a substituted or unsubstituted $C_3$-$C_{20}$ heterocycloalkyl, and combinations thereof.

$R_1$ and $R_2$ may form a substituted or unsubstituted $C_7$-$C_{20}$ fused ring or a substituted or unsubstituted $C_5$-$C_{20}$ fused heteroring.

When $R_1$ may be a substituted or unsubstituted $C_1$-$C_{15}$ alkyl, a substituted or unsubstituted $C_2$-$C_{16}$ alkenyl, a substituted or unsubstituted $C_2$-$C_{16}$ alkynyl, a substituted or unsubstituted $C_7$-$C_{18}$ arylalkyl, a substituted or unsubstituted $C_1$-$C_{20}$ heteroalkyl, a substituted or unsubstituted $C_3$-$C_{20}$ heteroarylalkyl, a substituted or unsubstituted $C_3$-$C_{15}$ cycloalkyl, a substituted or unsubstituted $C_3$-$C_{15}$ cycloalkenyl, a substituted or unsubstituted $C_6$-$C_{15}$ cycloalkynyl, or a substituted or unsubstituted $C_3$-$C_{20}$ heterocycloalkyl, the mixture may further include a hydrogen donor compound.

The hydrogen donor compound may be selected from the group consisting of 2,4-dimethyl-3-pentanol, 2,6-dimethyl-4-heptanol, formic acid, and mixtures thereof.

The metal catalyst may be selected from the group consisting of palladium black, palladium supported on a carrier, and mixtures thereof, and the carrier is selected from the group consisting of carbon, barium carbonate, calcium carbonate, aluminum oxyhydroxide, and combinations thereof.

According to one embodiment, palladium supported on aluminum oxyhydroxide may be appropriate for the metal catalyst.

The metal catalyst is used in an amount of 0.01 to 0.12 mole equivalent based on 1 mole equivalent of the amine compound.

The acyl donor compound is used in an amount of 1.7 to 3 mole equivalent based on 1 mole equivalent of the amine compound.

The biocatalyst may be selected from the group consisting of a fixed *Pseudomonas cepacia* lipase, a fixed *Candida antarctica* lipase, and mixtures thereof.

The biocatalyst may be used in an amount of 15 to 150 g based on 1 mole of the amine compound.

The chiral amide compound preparation process may be performed at a room temperature of up to 110° C.

The chiral amide compound preparation process may be performed under an inert gas atmosphere. According to another embodiment, when $R_1$ is a substituted or unsubstituted $C_1$-$C_{15}$ alkyl, a substituted or unsubstituted $C_2$-$C_{16}$ alkenyl, a substituted or unsubstituted $C_2$-$C_{16}$ alkynyl, a substituted or unsubstituted $C_7$-$C_{18}$ arylalkyl, a substituted or unsubstituted $C_1$-$C_{20}$ heteroalkyl, a substituted or unsubstituted $C_3$-$C_{20}$ heteroarylalkyl, a substituted or unsubstituted $C_3$-$C_{15}$ cycloalkyl, a substituted or unsubstituted $C_3$-$C_{15}$ cycloalkenyl, a substituted or unsubstituted $C_6$-$C_{15}$ cycloalkynyl, or a substituted or unsubstituted $C_3$-$C_{20}$ heterocycloalkyl, the chiral amide compound preparation process may be performed under a hydrogen atmosphere.

The mixture may be included at a concentration of 0.1 to 0.6M in an organic solvent.

The hydrolysis process may be performed using an acid solution.

According to another embodiment, chiral amines prepared in accordance with the above method may be provided.

In this specification, when specific description is not provided, "an alkyl" refers to a $C_1$-$C_{15}$ alkyl, "an alkenyl" refers to a $C_2$-$C_{16}$ alkenyl, "an alkynyl" refers to a $C_2$-$C_{16}$ alkynyl, "an aryl" refers to a $C_6$-$C_{18}$ aryl, "an arylalkyl" refers to a $C_7$-$C_{18}$ arylalkyl, "a heteroalkyl" refers to a $C_1$-$C_{20}$ heteroalkyl, "a heterocycle" refers to a $C_2$-$C_{20}$ heterocycle, "a heteroarylalkyl" refers to a $C_3$-$C_{20}$ heteroarylalkyl, "a cycloalkyl" refers to a $C_3$-$C_{15}$ cycloalkyl, "a cycloalkenyl" refers to a $C_3$-$C_{15}$ cycloalkenyl, "a cycloalkynyl" refers to a $C_6$-$C_{15}$ cycloalkynyl, "a heterocycloalkyl" refers to a $C_3$-$C_{20}$ heterocycloalkyl, and "an alkoxy" refers to a $C_1$-$C_{20}$ alkoxy.

The term "substituted" refers to hydrogen of the compound being substituted with a substituent selected from the group consisting of halogen (F, Br, Cl, or I), hydroxy, alkoxy, nitro, amino, azido, amidino, cyano, isocyano, cyanato, thiocyanato, hydrazino, hydrazono, carbonyl, carbamyl, thiocarbamyl, thiol, mesyl, ester, carboxyl, or a salt thereof, sulfonic acid or a salt thereof, phosphoric acid or a salt thereof, a $C_1$-$C_{15}$ alkyl, a $C_2$-$C_{16}$ alkenyl, a $C_2$-$C_{16}$ alkynyl, a $C_6$-$C_{18}$ aryl, a $C_7$-$C_{18}$ arylalkyl, a $C_1$-$C_{20}$ heteroalkyl, a $C_2$-$C_{20}$ heterocycle, a $C_3$-$C_{20}$ heteroarylalkyl, a $C_3$-$C_{15}$ cycloalkyl, a $C_3$-$C_{15}$ cycloalkenyl, a $C_6$-$C_{15}$ cycloalkynyl, a $C_3$-$C_{20}$ heterocycloalkyl, and combinations thereof.

DETAILED DESCRIPTION OF THE INVENTION

The present invention can provide chiral amines prepared by introducing a new metal catalyst with high reuse efficiency into a dynamic kinetic resolution method, so that commercially-available as well as benzyl amine-based various aliphatic amines can be used as a substrate. In addition, the present invention can provide chiral amines with excellent synthesis yield and high optical purity in a short reaction time by using a mixed catalyst of a metal catalyst and a biocatalyst. In particular, a method of synthesizing chiral amines according to the present invention is a general-purpose method, and thereby, the method is distinguished from a conventional method.

In other words, a method of preparing a chiral amine according to one embodiment of the present invention includes: reacting an amine compound having the following Formula 1, a metal catalyst, a biocatalyst including a lipase, and an acyl donor compound represented by the following Formula 2 in an organic solvent to obtain a chiral amide compound represented by the following Formula 3 (S1); and hydrolyzing the chiral amide compound to obtain a chiral amine represented by the following Formula 4 (S2).

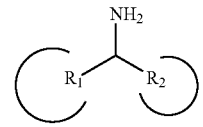

[Chemical Formula 1]

$R_3CO_2R_4$,

[Chemical Formula 2]

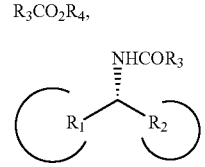

[Chemical Formula 3]

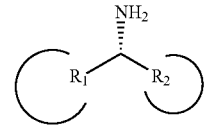

[Chemical Formula 4]

Wherein, in the above Formulae 1 to 4, $R_1$ and $R_2$ are connected to each other to form a ring, or are independently selected from the group consisting of hydroxyl, nitro, amino, azido, amidino, cyano, isocyano, cyanato, thiocyanato, hydrazino, hydrazono, carbonyl, carbamyl, thiocarbamyl, thiol, mesyl, a substituted or unsubstituted ester, carboxyl, or a salt thereof, sulfonic acid or a salt thereof, phosphoric acid or a salt thereof, a substituted or unsubstituted $C_1$-$C_{15}$ alkyl, a substituted or unsubstituted $C_2$-$C_{16}$ alkenyl, a substituted or unsubstituted $C_2$-$C_{16}$ alkynyl, a substituted or unsubstituted $C_6$-$C_{18}$ aryl, a substituted or unsubstituted $C_7$-$C_{18}$ arylalkyl, a substituted or unsubstituted $C_1$-$C_{20}$ heteroalkyl, a substituted or unsubstituted $C_2$-$C_{20}$ heterocycle, a substituted or unsubstituted $C_3$-$C_{20}$ heteroarylalkyl, a substituted or unsubstituted $C_3$-$C_{15}$ cycloalkyl, a substituted or unsubstituted $C_3$-$C_{15}$ cycloalkenyl, a substituted or unsubstituted $C_6$-$C_{15}$ cycloalkynyl, a substituted or unsubstituted $C_3$-$C_{20}$ heterocycloalkyl, and combinations thereof, wherein $R_1$ has a bigger steric size than $R_2$, $R_3$ and $R_4$ are independently selected from the group consisting of hydroxyl, nitro, amino, azido, amidino, cyano, isocyano, cyanato, thiocyanato, hydrazino, hydrazono, carbonyl, carbamyl, thiocarbamyl, thiol, mesyl, a substituted or unsubstituted ester, carboxyl, or a salt thereof, sulfonic acid or a salt thereof, phosphoric acid or a salt thereof, a substituted or unsubstituted $C_1$-$C_{15}$ alkyl, a substituted or unsubstituted $C_{16}$-$C_{16}$ alkenyl, a substituted or unsubstituted $C_2$-$C_{16}$ alkynyl, a substituted or unsubstituted $C_6$-$C_{18}$ aryl, a substituted or unsubstituted $C_7$-$C_{18}$ arylalkyl, a substituted or unsubstituted $C_1$-$C_{20}$ heteroalkyl, a substituted or unsubstituted $C_2$-$C_{20}$ heterocycle, a substituted or unsubstituted $C_3$-$C_{20}$ heteroarylalkyl, a substituted or unsubstituted $C_3$-$C_{15}$ cycloalkyl, a substituted or unsubstituted $C_3$-$C_{15}$ cycloalkenyl, a substituted or unsubstituted $C_6$-$C_{15}$ cycloalkynyl, a substituted or unsubstituted $C_3$-$C_{20}$ heterocycloalkyl, and combinations thereof.

Hereinafter, a method of manufacturing chiral amines according to the present invention is illustrated step by step in more detail.

First of all, a chiral amide compound is prepared by reacting a mixture including an amine compound as a starting material and a substrate, a metal catalyst for racemizing the amine compound, a biocatalyst containing a lipase stereoselectively acylating the racemic amine compound, and an acyl donor compound in an organic solvent (S1).

Further illustrating each component of the mixture, the amine compound as a starting material and a substrate may include various aliphatic amine compounds, and appropriately, an amine compound represented by the following Formula 1.

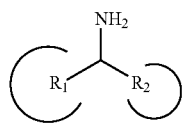

[Chemical Formula 1]

Herein, $R_1$ and $R_2$ are connected to each other to form a ring, or are independently selected from the group consisting of hydroxyl, nitro, amino, azido, amidino, cyano, isocyano, cyanato, thiocyanato, hydrazino, hydrazono, carbonyl, carbamyl, thiocarbamyl, thiol, mesyl, a substituted or unsubstituted ester, carboxyl, or a salt thereof, sulfonic acid or a salt thereof, phosphoric acid or a salt thereof, a substituted or unsubstituted $C_1$-$C_{15}$ alkyl, a substituted or unsubstituted $C_2$-$C_{16}$ alkenyl, a substituted or unsubstituted $C_2$-$C_{16}$ alkynyl, a substituted or unsubstituted $C_6$-$C_{18}$ aryl, a substituted or unsubstituted $C_7$-$C_{18}$ arylalkyl, a substituted or unsubstituted $C_1$-$C_{20}$ heteroalkyl, a substituted or unsubstituted $C_2$-$C_{20}$ heterocycle, a substituted or unsubstituted $C_3C_{20}$ heteroarylalkyl, a substituted or unsubstituted $C_3$-$C_{15}$ cycloalkyl, a substituted or unsubstituted $C_3$-$C_{15}$ cycloalkenyl, a substituted or unsubstituted $C_6$-$C_{15}$ cycloalkynyl, a substituted or unsubstituted $C_3$-$C_{20}$ heterocycloalkyl, and combinations thereof, wherein $R_1$ has a bigger steric size than $R_2$, $R_3$ and $R_4$ are independently selected from the group consisting of hydroxyl, nitro, amino, azido, amidino, cyano, isocyano, cyanato, thiocyanato, hydrazino, hydrazono, carbonyl, carbamyl, thiocarbamyl, thiol, mesyl, a substituted or unsubstituted ester, carboxyl, or a salt thereof, sulfonic acid or a salt thereof, phosphoric acid or a salt thereof, a substituted or unsubstituted $C_1$-$C_{15}$ alkyl, a substituted or unsubstituted $C_2$-$C_{16}$ alkenyl, a substituted or unsubstituted $C_2$-$C_{16}$ alkynyl, a substituted or unsubstituted $C_6$-$C_{18}$ aryl, a substituted or unsubstituted $C_7$-$C_{18}$ arylalkyl, a substituted or unsubstituted $C_1$-$C_{20}$ heteroalkyl, a substituted or unsubstituted $C_2$-$C_{20}$ heterocycle, a substituted or unsubstituted $C_3$-$C_{20}$ heteroarylalkyl, a substituted or unsubstituted $C_3$-$C_{15}$ cycloalkyl, a substituted or unsubstituted $C_3$-$C_{15}$ cycloalkenyl, a substituted or unsubstituted $C_6$-$C_{15}$ cycloalkynyl, a substituted or unsubstituted $C_3$-$C_{20}$ heterocycloalkyl, and combinations thereof.

$R_1$ and $R_2$ may form a substituted or unsubstituted $C_7$-$C_{20}$ fused ring or a substituted or unsubstituted $C_5$-$C_{20}$ fused heteroring.

In the above Formulae, examples of the unsubstituted $C_1$-$C_{15}$ alkyl include methyl, ethyl, propyl, isopropyl, isobutyl, (sec)-butyl, pentyl, iso-amyl, hexyl, and so on.

The substituted $C_1$-$C_{15}$ alkyl may include substituents selected from the group consisting of halogen (F, Cl, Br, or I), hydroxy, alkoxy, nitro, amino, azido, amidino, cyano, isocyano, cyanato, thiocyanato, hydrazino, hydrazono, carbonyl, carbamyl, thiocarbamyl, thiol, mesyl, a substituted or unsubstituted ester, carboxyl, or a salt thereof, sulfonic acid or a salt thereof, phosphoric acid or a salt thereof, a substituted or unsubstituted $C_1$-$C_{15}$ alkyl, a substituted or unsubstituted $C_2$-$C_{16}$ alkenyl, a substituted or unsubstituted $C_2$-$C_{16}$ alkynyl, a substituted or unsubstituted $C_6$-$C_{18}$ aryl, a substituted or unsubstituted $C_7$-$C_{18}$ arylalkyl, a substituted or unsubstituted $C_1$-$C_{20}$ heteroalkyl, a substituted or unsubstituted $C_2$-$C_{20}$ heterocycle, a substituted or unsubstituted $C_3$-$C_{20}$ heteroarylalkyl, a substituted or unsubstituted $C_3$-$C_{15}$ cycloalkyl, a substituted or unsubstituted $C_3$-$C_{15}$ cycloalkenyl, a substituted or unsubstituted $C_6$-$C_{15}$ cycloalkynyl, and a substituted or unsubstituted $C_3$-$C_{20}$ heterocycloalkyl instead of at least one hydrogen.

The unsubstituted $C_2$-$C_{16}$ alkenyl or alkynyl refers to a group including a carbon double bond or triple bond in the middle or terminal of the above-defined alkyl. Examples of the alkenyl or alkynyl include vinyl, propenyl, butenyl, hexenyl, ethynyl, and so on. At least one hydrogen of alkenyl or alkynyl can be substituted with the same substituent as for the alkyl.

The aryl may be used independently or in combination, and refers to a $C_6$-$C_{18}$ carbocycle aromatic system including at least one ring. The ring may be attached as a pendent group or fused to the $C_6$-$C_{18}$ carbocycle aromatic system. The aryl refers to aromatic radicals such as phenyl, naphthyl, tetrahydronapthyl, indian, cyclopentadienyl, and biphenyl. At least one hydrogen of the aryl can be substituted with the same substituent as for the alkyl.

The arylalkyl refers to an aryl including a $C_1$ to $C_5$ lower alkyl radical such as such as methyl, ethyl, propyl, and so on. The aryl is the same as above defined. Examples of the arylalkyl are benzyl, phenylethyl, and so on. At least one hydrogen of the arylalkyl can be substituted with the same substituent as for the alkyl.

The heteroalkyl refers to an alkyl including nitrogen, sulfur, oxygen, or phosphorus. The alkyl is the same as above defined. Examples of heteroalkyl include alkoxy such as methoxy, ethoxy, propoxy, isopropoxy, butoxy, sec-butoxy, t-butoxy, benzyloxy, naphthyloxy, triphenylmethoxy, and so on; acyl such as acetyl, propionyl, butyryl, isobutyryl, valeryl, pivaloyl and so on; alkylamino such as methylamino, dimethylamino, and so on; or an alkylthio such as methylthio, ethylthio, and so on.

At least one hydrogen of the heteroalkyl can be substituted with the same substituent as for the alkyl. Examples of the substituted heteroalkyl may include haloalkoxyradical such as fluoromethoxy, chloromethoxy, trifluoromethoxy, trifluoroethoxy, fluoroethoxy, and fluoropropoxypropoxy.

The heterocycle may include 4 to 23 atoms of a cyclic radical including 1, 2, or 3 heteroatoms selected from a group consisting of N, O, P, and S and the remaining atoms may be carbon. The term also refers to a cyclic aromatic radical where heteroatoms in a ring formation are oxidized or become quaternary to form, for example, N-oxide or a quaternary salt. Specific examples may include, but are not limited to, thienyl, puryl, benzothienyl, pyridyl, prazinyl, pyrimidinyl, pyridazinyl, quinolinyl, quinoxalinyl, imidazolyl, puranyl, benzopuranyl, thiazolyl, isoxazolyl, benzisoxazolyl, benzimidazolyl, triazolyl, pyrazolyl, pyrrolyl, indolyl, pyridonyl, N-alkyl-2-pyridonyl, pyrazinonyl, pyridazinonyl, pyrimidinonyl, oxazolonyl, and N-oxide thereof (for example, pyridyl N-oxide, quinolinyl N-oxide), and quaternary salt thereof. At least one hydrogen of the heterocycle can be substituted with the same substituent as for the alkyl.

The heteroarylalkyl refers to a combined group of a heterocycle and an alkyl. At least one hydrogen of the heteroarylalkyl can be substituted with the same substituent as for the alkyl.

The cycloalkyl and cycloalkenyl may be a $C_3$-$C_{15}$ cyclic radical. At least one hydrogen of the cycloalkyl and cycloalkenyl can be substituted with the same substituent as for the alkyl.

The cycloalkynyl is a $C_6$-$C_{15}$ cyclic radical. At least one hydrogen of the cycloalkynyl can be substituted with the same substituent as for the alkyl.

The heterocycloalkyl may include 4 to 23 atoms of a cyclic radical including 1, 2, or 3 heteroatoms selected from a group consisting of N, O, P, and S, and the remaining atoms may be carbon. That is to say, hydrogens of the cycloalkyl may be substituted with an alkyl, and a heteroatom is included. Examples of the cycloalkyl are aziridinyl, pyrrolidinyl, piperidinyl, piperazinyl, morpholinyl, thiomorpholinyl, tetrahydrofuranyl, tetrahydrothiofuranyl, tetrahydropyranyl, pyranyl, and so on. At least one hydrogen of the heterocycloalkyl can be substituted with the same substituent as for the alkyl.

The fused ring may include 7 to 20 atoms in a bicyclic or tricyclic aromatic radical where $R_1$ and $R_2$ are linked to form a ring and the aryl ring may be substituted. For example, specific examples include indanyl, indenyl, dihydronaphthyl, tetrahydronaphthyl, etc. At least one hydrogen of the fused ring can be substituted with the same substituent as for the alkyl.

The hetero-fused ring may include 6 to 23 atoms in a bicyclic or tricyclic radical including 1, 2, or 3 heteroatoms selected from a group consisting of N, O, P, and S, with the remaining atoms in the radical being carbon. The term also means a cyclic aromatic radical where heteroatoms in the ring are oxidized or become quaternary to form, for example, an N-oxide or a quaternary salt. Specific examples may include, but are not limited to, benzothienyl, cumaryl, quinolinyl, quinoxalinyl, benzopuranyl, benzothiazolyl, benzoisoxazolyl, benzoimidazolyl, indolyl, benzopyridonyl, N-alkyl-2-benzopyridonyl, benzopyrazinonyl, benzopyridazinonyl, benzopyrimidinonyl, benzooxazolonyl, an N-oxide (for example, pyridyl N-oxide, quinoliny N-oxide), and a quaternary salt. At least one hydrogen of the hetero-fused ring can be substituted with the same substituent as for the alkyl.

The metal catalyst plays a role of racemizing amine and promotes racemization through oxidation and reduction of an amine compound represented by the above Formula 1.

The metal catalyst may include palladium black not supported on a carrier, palladium supported on a carrier (atom value=0), or mixtures thereof. When palladium is supported on a carrier, the carrier may include carbon, barium carbonate, calcium carbonate, aluminum hydroxide, or aluminum oxide. These catalysts have excellent thermal stability, and thereby can be reused at a temperature of 100° C.

Among these catalysts, palladium supported on a carrier is easier to handle than the others. In addition, palladium supported on aluminum oxyhydroxide can be better the others, in that it cannot only be reused but also has a rapid reaction speed and can acquire a reaction product with high purity.

The metal catalyst may be supported in an amount of 0.5 to 5 wt % based on 100 parts by weight of a carrier.

The metal catalyst may be used in an amount of 0.01 to 0.12 mole equivalent based on 1 mole equivalent of an amine compound represented by Chemical Formula 1. When the metal catalyst is included in an amount of 0.01 mole equivalent or less based on 1 mole equivalent of an amine compound, it may have a problem of slow reaction speed. On the contrary, when it is included in an amount of 0.12 mole equivalent or more, it may be inefficient. Herein, the amount of the metal catalyst refers to only the amount of a metal except for a carrier.

The biocatalyst including a lipase plays a role of stereoselectively acylating a racemic compound under an acyl donor in an organic solvent. In other words, the biocatalyst including a lipase plays a role of promoting reaction of selectively acylating only a (R)-compound, which is an enantiomer converted into a racemic compound by a metal catalyst.

Examples of the biocatalyst including a lipase are a pseudomonas cepacia lipase that can be bought as a fixed type (for example, lipase PS-C/D, Japanese Amino Co.), a candida antarctica lipase (for example, Novozym 435, Novo Nordisk Korea Co.), or mixtures thereof The biocatalyst is also thermally stable and can be reused at a temperature of 100° C.

The biocatalyst is included in an amount of 15 to 150 g based on 1 mole of an amine compound represented by Chemical Formula 1. When the biocatalyst is included in an amount of 15 g or less based on 1 mole of an amine compound represented by Chemical Formula 1, it may have a problem of a slow reaction speed. On the contrary, when it is included in an amount of 150 g or more, it may be inefficient.

The acyl donor compound for acylating an amine compound participates in acylation reaction of amine by a lipase as a biocatalyst, and thereby produces a chiral amide.

This acyl donor compound may include a compound represented by the following Formula 2.

    [Chemical Formula 2]

Wherein, in the above formula, $R_3$ and $R_4$ are independently selected from the group consisting of hydroxyl, nitro, amino, azido, amidino, cyano, isocyano, cyanato, thiocyanato, hydrazino, hydrazono, carbonyl, carbamyl, thiocarbamyl, thiol, mesyl, a substituted or unsubstituted ester, carboxyl, or a salt thereof, sulfonic acid or a salt thereof, phosphoric acid or a salt thereof, a substituted or unsubstituted $C_1$-$C_{15}$ alkyl, a substituted or unsubstituted $C_2$-$C_{16}$ alkenyl, a substituted or unsubstituted $C_2$-$C_{16}$ alkynyl, a substituted or unsubstituted $C_6$-$C_{18}$ aryl, a substituted or unsubstituted $C_7$-$C_{18}$ arylalkyl, a substituted or unsubstituted $C_1$-$C_{20}$ heteroalkyl, a substituted or unsubstituted $C_2$-$C_{20}$ heterocycle, a substituted or unsubstituted $C_3$-$C_{20}$ heteroarylalkyl, a substituted or unsubstituted $C_3$-$C_{15}$ cycloalkyl, a substituted or unsubstituted $C_3$-$C_{15}$ cycloalkenyl, a substituted or unsubstituted $C_6$-$C_{15}$ cycloalkynyl, a substituted or unsubstituted $C_3$-$C_{20}$ heterocycloalkyl, and combinations thereof.

The above functional groups have the same substituents as above described for the alkyl.

The acyl donor compound represented by the above Chemical Formula 2 may be included in an amount of 1.7 to 3 mole equivalent based on 1 mole equivalent of an amine compound represented by the above Formula 1. When the acyl donor compound represented by the above Chemical Formula 2 is included in an amount of 1.7 mole equivalent or less based on 1 mole equivalent of the amine compound, it may have a problem of a slow reaction speed. On the contrary, when it is included in an amount of 3 mole equivalent or more, it may cause inefficiency.

Then, an amine compound with the aforementioned Chemical Formula 1, a metal catalyst, a biocatalyst including lipase, and an acyl donor compound represented by Chemical Formula 2 is put in a reaction container. An organic solvent is added thereto, and thereafter, the components are mixed for reaction in the organic solvent.

According to the embodiment of the present invention, the organic solvent has no particular limit. However, considering that enzyme catalyst reaction like a lipase has an influence from a solvent in terms of a product synthesis yield and stereoselectivity, it may include aromatic hydrocarbons such as benzene, toluene, and the like; $C_5$-$C_{10}$ alkanes; $C_5$-$C_{10}$ cycloalkane; ethers such as tetrahydrofuran, dioxane, and the like; $C_2$-$C_{10}$ dialkylethers such as diethylether, di-isopropylether, t-butylmethylether, and the like; esters with $C_3$-$C_{10}$ alkyl substitutents such as ethylacetate, propylacetate, and ethylpropinonate; $C_2$-$C_{10}$ cyanoalkanes such as acetonitrile, propinonitrile, and the like; $C_3$-$C_{10}$ dialkylketone such as acetone, methylethylketone, and the like; aprotic solvents such as dichloromethane, chloroform, carbon tetrachloride, and the like (polar aprotic solvent); or $C_4$-$C_{10}$ tertiary alcohols such as tert-butanol or 3-methyl-3-pentenol, which is strongly hydrophobic; and the like. In addition, it may include a room temperature ionic liquid such as 1-methyl-3-ethylimidazolium tetrafluoroborate or 1-methyl-3-butylimidazolium hexafluorophosphate.

The solvent may be regulated to include a solute, which is a mixture including an amine compound represented by Chemical Formula 1, a metal catalyst, a biocatalyst, and an acyl donor compound represented by Chemical Formula 2, at a concentration of 0.1 to 0.6M. When the solute is included beyond the concentration range, it may have a slow reaction speed or a by-product.

In addition, the reaction can be appropriately performed under an inert gas atmosphere such as nitrogen or argon.

In the above amine compound of Formula 1, when $R_1$ is a substituted or unsubstituted $C_1$-$C_{15}$ alkyl, a substituted or unsubstituted $C_2$-$C_{16}$ alkenyl, a substituted or unsubstituted $C_2$-$C_{16}$ alkynyl, a substituted or unsubstituted $C_7$-$C_{18}$ arylalkyl, a substituted or unsubstituted $C_1$-$C_{20}$ heteroalkyl, a substituted or unsubstituted $C_3$-$C_{20}$ heteroarylalkyl, a substituted or unsubstituted $C_3$-$C_{15}$ cycloalkyl, a substituted or unsubstituted $C_3$-$C_{15}$ cycloalkenyl, a substituted or unsubstituted $C_6$-$C_{15}$ cycloalkynyl, or a substituted or unsubstituted $C_3$-$C_{20}$ heterocycloalkyl, the chiral amide compound preparation process is performed under a hydrogen atmosphere in order to promote a reduction reaction of the amine compound, rather than under the inert gas atmosphere. Alternatively the chiral amide compound preparation process is performed in condition of addition of a hydrogen donor compound.

The hydrogen donor compound is a $C_5$-$C_{12}$ alcohol with alkyl substitutents such as 2,4-dimethyl-3-pentanol, 2,6-dimethyl-4-heptanol, formic acid, and mixtures thereof.

In addition, the hydrogen donor compound is removed after acquiring a chiral amide. Herein, the hydrogen donor compound can be easily removed when it is added under a normal pressure condition.

The hydrogen donor compound may be used in an amount of 1 to 10 mole equivalent based on 1 mole equivalent of an amine compound represented by the above Formula 1. When it is used in amount of 1 mole equivalent or less, it may cause a slow reaction speed. On the contrary, when it is used in an amount of 10 mole equivalent or more, it may have an inefficiency problem.

In addition, the reaction may be performed from room temperature up to 110° C. However, according to another embodiment, it can be performed at a temperature of 60 to 110° C.

When the reaction is completed under the aforementioned conditions, a chiral amide compound represented by the following Formula 3 can be acquired after common filtering and refining processes.

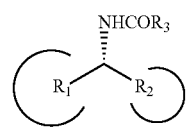

[Chemical Formula 3]

In the above Formula 3, $R_1$, $R_2$, and $R_3$ are the same as aforementioned.

The prepared chiral amide compound can be examined with $^1$H-NMR and $^{13}$C-NMR to identify its chemical structure. Its optical purity can be identified by using a high speed chiral liquid chromatography. Herein, a column includes Whelk-O1 and Chiraldex OD-H.

The chiral amide compound represented by Chemical Formula 3 can be prepared as follows. A first step (S1) includes a dynamic kinetic resolution reaction of various amine compounds represented by Chemical Formula 1 as a substrate in an organic solvent by using a mixed catalyst of a metal catalyst and a biocatalyst in a reaction container. The reaction is not multi-step but a one-pot reaction where all reactants are simultaneously reacted with one another.

In addition, when $R_1$ of Chemical Formula 1 in the reaction is not a substituted or unsubstituted $C_6$-$C_{18}$ aryl or a substituted or unsubstituted $C_2$-$C_{20}$ heterocycle, the reaction can be simultaneously performed in one pot under a hydrogen atmosphere or by adding a hydrogen donor compound thereto.

Next, a chiral amine of the following Formula 4 is prepared by hydrolyzing the prepared chiral amide compound (S2).

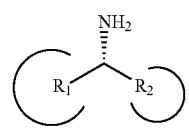

[Chemical Formula 4]

In the above Formula 4, $R_1$ and $R_2$ are the same as aforementioned.

The hydrolysis can be performed by using an acid solution such as hydrochloric acid and the like. The hydrolysis process using a hydrochloric acid is very well-known in this related field and does not need a detailed description here.

According to one embodiment of the present invention, a method of preparing a chiral amine-based compound has the following features: (a) introducing into a dynamic kinetic resolution reaction a new metal catalyst such as a palladium catalyst supported on aluminum oxyhydroxide, which has high reuse efficiency and thereby can be repeatedly reused; (b) variously using commercially-available as well as benzyl amine-based aliphatic amines; (c) repeatedly reusing metal catalyst and a biocatalyst for reaction; and (d) being a one-pot reaction in which all reaction steps are performed in one container.

In addition, a chiral amine prepared according to a manufacturing method of the present invention can be used for various chiral drugs or an intermediate material for fine chemistry products.

Hereinafter, the present invention is illustrated in more detail with reference to the following examples but is not limited thereto.

EXAMPLE 1

A mixture was prepared by mixing 97 mg of α-methylbenzylamine, 99 mg of Pd/AlO(OH), 96 mg of Novozym-435 (candida antarctica lipase), 211 mg of ethyl acetate, and 560 mg of a molecular sieve 4 Å for promoting filtration of a target product. Then, 8 mL of toluene was added to the mixture in a schlenk flask. The resulting mixture was agitated for reaction at 70° C. for 3 days.

When the reaction was complete, a glass-filter was used to obtain a metal catalyst and a biocatalyst filtrate. The filtrate was condensed, and then, column chromatography was performed thereto to separate a product by using a mixture including silica gel and ethylacetate/hexane in a volume ratio of 1:1.

The acquired product is shown in the following Table 1. Its optical purity was measured by using high performance liquid chromatography equipped with a chiral column. The product, (R)-amide, had a yield of 92% and optical purity of 98% ee (enantiomeric excess).

EXAMPLE 8

A product was gained according to the same method as in Example 1, except for using 0.8 mmole of amine as a substrate instead of α-methylbenzylamine, as shown in the following Table 1.

Table 1 shows isolation yield and optical purity of chiral amines according to Examples 1 to 8.

TABLE 1

| Example | Substrate | Product | Isolation yield (%) | Optical purity (%) |
|---------|-----------|---------|---------------------|--------------------|
| 1 | NH$_2$, phenyl | NHAc, phenyl | 92 | 98 |
| 2 | NH$_2$, 4-methylphenyl | NHAc, 4-methylphenyl | 91 | 97 |
| 3 | NH$_2$, 4-methoxyphenyl (OMe) | NHAc, 4-methoxyphenyl (OMe) | 93 | 98 |
| 4 | NH$_2$, 4-CF$_3$-phenyl | NHAc, 4-CF$_3$-phenyl | 95 | 98 |
| 5 | NH$_2$, ethyl/phenyl | NHAc, ethyl/phenyl | 90 | 98 |
| 6 | H$_2$N-indanyl | AcHN-indanyl | 88 | 99 |

TABLE 1-continued

| Example | Substrate | Product | Isolation yield (%) | Optical purity (%) |
|---------|-----------|---------|---------------------|--------------------|
| 7 | 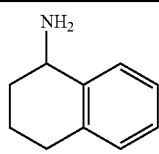 | 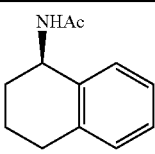 | 86 | 97 |
| 8 | 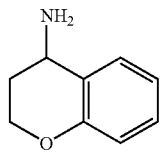 | 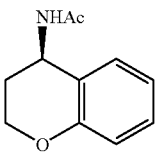 | 94 | 98 |

EXAMPLE 9

A mixture was prepared by mixing 36 mg of α-methylbenzylamine, 36 mg of Pd/AlO(OH), 4.5 mg of Novozym-435, and 72 mg of ethyl methoxyacetate, and then, 3 mL of toluene was added thereto in a schlenk flask. The resulting mixture was agitated for reaction at 70° C. for 3 days.

When the reaction was complete, a glass-filter was used to obtain a catalyst filtrate. The filtrate was concentrated, and then, column chromatography was performed to separate a product by using a mixture including silica gel and ethylacetate/hexane in a volume ratio of 1:1. The product is shown in the following Table 2.

Its optical purity was measured by using high performance liquid chromatography equipped with a chiral column. The produced (R)-amide had a yield of 98% and optical purity of 99% ee.

EXAMPLES 10 TO 16

A product was gained according to the same method as in Example 9, except for using 0.3 mmole of amine as a substrate instead of α-methylbenzylamine, as shown in the following Table 2.

Table 2 shows isolation yield and optical purity of the chiral amides according to Examples 9 to 16.

TABLE 2

| Example | Substrate | Product | Isolation yield (%) | Optical purity (%) |
|---------|-----------|---------|---------------------|--------------------|
| 9 | 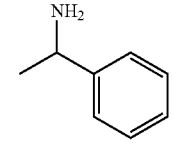 | 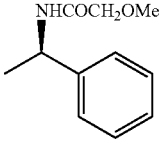 | 98 | 99 |
| 10 | 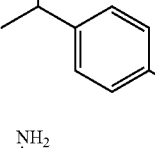 | 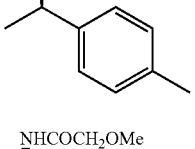 | 85 | 99 |
| 11 | 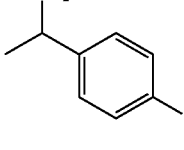 | 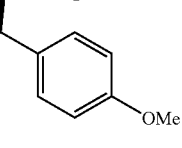 | 85 | 98 |
| 12 | 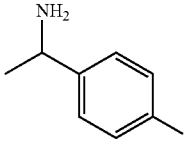 | 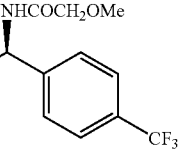 | 99 | 99 |

TABLE 2-continued

| Example | Substrate | Product | Isolation yield (%) | Optical purity (%) |
|---|---|---|---|---|
| 13 | NH₂ (1-phenylpropyl amine) | NHCOCH₂OMe | 96 | 99 |
| 14 | H₂N-indanyl | NHCOCH₂OMe | 87 | 97 |
| 15 | NH₂-tetrahydronaphthyl | NHCOCH₂OMe | 84 | 99 |
| 16 | NH₂-chromanyl | NHCOCH₂OMe | 92 | 99 |

EXAMPLE 17

2 mL of toluene was added to a mixture including 30 mg of 2-amino-2-phenylacetamide, 60 mg of Pd/AlO(OH), 24 mg of Novozym-435, and 47 mg of ethylmethoxyacetate in a schlenk flask. The resulting product was agitated for reaction at 60° C. for 3 days.

When the reaction was complete, a glass-filer was used to obtain a catalyst filtrate. The filtrate was concentrated, and then, column chromatography was performed to separate a product prepared by using a mixture including silica gel and methylene chloride/methanol in a volume ratio of 10:1. The product is shown in the following Table 3.

Its optical purity was measured by using high performance liquid chromatography equipped with a chiral column. The produced (S)-amide had a yield of 98% and an optical purity of 98% ee.

EXAMPLES 18 TO 21

A product was gained according to the same method as in Example 17, except for using 0.2 mmole of amine as a substrate instead of 2-amino-2-phenylacetamide, as shown in the following Table 3.

Table 3 shows isolation yield and optical purity of the chiral amides according to Examples 17 to 21.

TABLE 3

| Example | Substrate | Product | Isolation yield (%) | Optical purity (%) |
|---|---|---|---|---|
| 17 | 2-amino-2-phenylacetamide | (S)-NHCOCH₂OMe amide | 98 | 98 |
| 18 | 2-amino-2-(4-fluorophenyl)acetamide | (S)-NHCOCH₂OMe amide | 91 | 97 |

TABLE 3-continued

| Example | Substrate | Product | Isolation yield (%) | Optical purity (%) |
|---|---|---|---|---|
| 19 | H₂N-C(=O)-CH(NH₂)-C₆H₄-OMe (para) | H₂N-C(=O)-CH(NHCOCH₂OMe)-C₆H₄-OMe (para) | 91 | 97 |
| 20 | H₂N-C(=O)-CH(NH₂)-C₆H₄-Cl (para) | H₂N-C(=O)-CH(NHCOCH₂OMe)-C₆H₄-Cl (para) | 88 | 98 |
| 21 | H₂N-C(=O)-CH(NH₂)-C₆H₄-CF₃ (para) | H₂N-C(=O)-CH(NHCOCH₂OMe)-C₆H₄-CF₃ (para) | 90 | 97 |

EXAMPLE 22

159 mg of ethyl acetate was added to a mixture including 90 mg of 1-methyl-3-phenylpropylamine, 891 mg of Pd/AlO(OH), and 72 mg of Novozym-435 in a schlenk flask. The resulting mixture was agitated for reaction under 1 atm of hydrogen gas at 100° C. for 4 hours.

When the reaction was complete, a glass-filter was used to obtain a catalyst filtrate. The filtrate was concentrated, and then, column chromatography was performed to separate a product by using a mixture including silica gel and ethylacetate/hexane in a volume ratio of 1:1. The product is shown in the following Table 4.

Its optical purity was measured by using high performance liquid chromatography equipped with a chiral column. Accordingly, the produced (R)-amide had a yield of 95% and optical purity of 98% ee.

EXAMPLES 23 TO 25

A product was gained according to the same method as in Example 22, except for using 0.6 mmole of amine as a substrate instead of 1-methyl-3-phenylpropylamine, as shown in the following Table 4.

The chiral amide according to Examples 23 to 25 was measured regarding isolation yield and optical purity. The results are shown in the following Table 4.

TABLE 4

| Example | Substrate | Product | Isolation yield (%) | Optical purity (%) |
|---|---|---|---|---|
| 22 | 1-methyl-3-phenylpropylamine (NH₂) | N-acetyl-1-methyl-3-phenylpropylamine (NHAc) | 95 | 98 |
| 23 | 1-phenylethylamine (NH₂) | N-acetyl-1-phenylethylamine (NHAc) | 93 | 99 |
| 24 | 2-octylamine (NH₂) | N-acetyl-2-octylamine (NHAc) | 92 | 98 |

TABLE 4-continued

| Example | Substrate | Product | Isolation yield (%) | Optical purity (%) |
|---|---|---|---|---|
| 25 | ![benzyl substrate with CONH2 and NH2] | ![benzyl product with CONH2 and NHAc] | 96 | 98 |

EXAMPLE 26

8 mL of toluene was added to a mixture including 90 mg of 1-methyl-3-phenylpropylamine, 891 mg of Pd/AlO(OH), 72 mg of Novozym-435, and 159 mg of ethyl acetate in a schlenk flask. The resulting mixture was agitated for reaction under 1 atm of hydrogen gas at 100° C. for 4 hours.

When the reaction was complete, a glass-filter was used to obtain a metal catalyst and a biocatalyst filtrate. The filtrate was analyzed by using GC and HPLC. The separated metal catalyst and biocatalyst were washed with ethyl acetate, and then dried under a vacuum for reuse.

The chiral amine according to Example 26 was measured regarding an amide conversion rate depending on its reuse frequency. The result is shown in Table 5.

TABLE 5

| Frequency of reuse | Conversion rate (%) | Resulting material (%) | Optical purity (%) |
|---|---|---|---|
| 1 | >99 | >98 | 99 |
| 2 | >99 | >98 | 99 |
| 3 | >99 | >98 | 98 |
| 4 | >99 | >98 | 97 |
| 5 | >99 | >98 | 96 |
| 6 | >99 | >98 | 95 |
| 7 | >99 | >98 | 94 |
| 8 | 99 | >98 | 93 |
| 9 | 93 | 93 | 93 |
| 10 | 89 | 89 | 92 |
| 11 | >99 | >98 | 95 |

As shown in Table 5, even when the metal catalyst and the biocatalyst were used 11 times, they had a high conversion rate of converting amine into chiral amide and turned out to gain amide with excellent optical purity.

In other words, the results from Tables 1 to 5 show that chiral amide with excellent optical purity (97-99% ee) can be yielded from amine even with a high yield (84-99%) by harmonizing palladium as a metal catalyst for racemization reaction and lipase as an enzyme for acylation reaction. Accordingly, the metal catalyst and enzyme turned out to be thermally stable and thereby able to be reused.

EXAMPLE 27

130 mg of (R)-1-phenylethylacetamide according to Example 22, 3 mL of 6N HCl, and 3 mL of methanol were poured into a round-bottomed flask with a reflux condenser, and then agitated together at 80° C. for 15 hours.

When the reaction was complete, the filtrate was concentrated to remove methanol. The resulting mixture solution was neutralized with 4N NaOH, and thereafter extracted with dichloromethane.

The product was measured regarding optical purity by using high performance liquid chromatography equipped with a chiral column. The produced (R)-amine had a yield of 98% and optical purity of 98% ee.

On the other hand, the present invention provides a method of preparing chiral amine into a stereoselective amide by mixing a metal catalyst and a biocatalyst.

In addition, the present invention includes a new technique of introducing a thermally-stable and reusable metal catalyst into a dynamic kinetic resolution to mix with a biocatalyst, and thereby, has an advantage of synthesizing chiral amine with excellent optical purity and a high yield.

Unlike a conventional method, the manufacturing method can use various commercially-available aliphatic amines as well as benzyl amine-based materials as a substrate, and thereby, is more applicable for synthesizing a amine with various structures. In addition, it has a feature of a one-pot reaction where all reaction steps are performed in one container and thereby can replace the conventional pure-chemical or biochemical synthesis methods.

In addition, chiral amines prepared according to the manufacturing method of the present invention can be effectively used as various chiral drugs or intermediate materials for a synthetic chemistry product.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A method of preparing a chiral amine comprising:
   reacting a mixture comprising an amine compound having the following Formula 1, a metal catalyst, a biocatalyst including a lipase, and an acyl donor compound having the following Formula 2 in an organic solvent to obtain a chiral amide compound having the following Formula 3; and
   hydrolyzing the chiral amide compound to obtain a chiral amine having the following Formula 4, wherein,

[Chemical Formula 1]

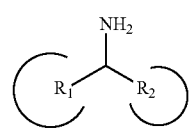

[Chemical Formula 2]

$R_3CO_2R_4$,

[Chemical Formula 3]

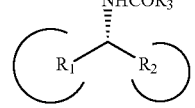

-continued

[Chemical Formula 4]

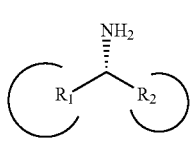

wherein, in the above Formulae 1 to 4, $R_1$ and $R_2$ are connected to each other to form a ring, or are independently selected from the group consisting of hydroxyl, nitro, amino, azido, amidino, cyano, isocyano, cyanato, thiocyanato, hydrazino, hydrazono, carbonyl, carbamyl, thiocarbamyl, thiol, mesyl, a substituted or unsubstituted ester, carboxyl, or a salt thereof, sulfonic acid or a salt thereof, phosphoric acid or a salt thereof, a substituted or unsubstituted $C_1$-$C_{15}$ alkyl, a substituted or unsubstituted $C_2$-$C_{16}$ alkenyl, a substituted or unsubstituted $C_2$-$C_{16}$ alkynyl, a substituted or unsubstituted $C_6$-$C_{18}$ aryl, a substituted or unsubstituted $C_7$-$C_{18}$ arylalkyl, a substituted or unsubstituted $C_1$-$C_{20}$ heteroalkyl, a substituted or unsubstituted $C_2$-$C_{20}$ heterocycle, a substituted or unsubstituted $C_3$-$C_{20}$ heteroarylalkyl, a substituted or unsubstituted $C_3$-$C_{15}$ cycloalkyl, a substituted or unsubstituted $C_3$-$C_{15}$ cycloalkenyl, a substituted or unsubstituted $C_6$-$C_{15}$ cycloalkynyl, a substituted or unsubstituted $C_3$-$C_{20}$ heterocycloalkyl, and combinations thereof, $R_3$ and $R_4$ are independently selected from the group consisting of hydroxyl, nitro, amino, azido, amidino, cyano, isocyano, cyanato, thiocyanato, hydrazino, hydrazono, carbonyl, carbamyl, thiocarbamyl, thiol, mesyl, a substituted or unsubstituted ester, carboxyl, or a salt thereof, sulfonic acid or a salt thereof, phosphoric acid or a salt thereof, a substituted or unsubstituted $C_1$-$C_{15}$ alkyl, a substituted or unsubstituted $C_2$-$C_{16}$ alkenyl, a substituted or unsubstituted $C_2$-$C_{16}$ alkynyl, a substituted or unsubstituted $C_6$-$C_{18}$ aryl, a substituted or unsubstituted $C_7$-$C_{18}$ arylalkyl, a substituted or unsubstituted $C_1$-$C_{20}$ heteroalkyl, a substituted or unsubstituted $C_2$-$C_{20}$ heterocycle, a substituted or unsubstituted $C_3$-$C_{20}$ heteroarylalkyl, a substituted or unsubstituted $C_3$-$C_{15}$ cycloalkyl, a substituted or unsubstituted $C_3$-$C_{15}$ cycloalkenyl, a substituted or unsubstituted $C_6$-$C_{15}$ cycloalkynyl, a substituted or unsubstituted $C_3$-$C_{20}$ heterocycloalkyl, and combinations thereof, wherein $R_1$ has a bigger steric size than $R_2$, and the metal catalyst is palladium supported on aluminum oxyhydroxide.

2. The method of claim 1, wherein $R_1$ and $R_2$ form a substituted or unsubstituted $C_7$-$C_{20}$ fused ring or a substituted or unsubstituted $C_5$-$C_{20}$ fused heteroring.

3. The method of claim 1, wherein, when $R_1$ is a substituted or unsubstituted $C_1$-$C_{15}$ alkyl, a substituted or unsubstituted $C_2$-$C_{16}$ alkenyl, a substituted or unsubstituted $C_2$-$C_{16}$ alkynyl, a substituted or unsubstituted $C_7$-$C_{18}$ arylalkyl, a substituted or unsubstituted $C_1$-$C_{20}$ heteroalkyl, a substituted or unsubstituted $C_3$-$C_{20}$ heteroarylalkyl, a substituted or unsubstituted $C_3$-$C_{15}$ cycloalkyl, a substituted or unsubstituted $C_3$-$C_{15}$ cycloalkenyl, a substituted or unsubstituted $C_6$-$C_{15}$ cycloalkynyl, or a substituted or unsubstituted $C_3$-$C_{20}$ heterocycloalkyl, the mixture further includes a hydrogen donor compound.

4. The method of claim 3, wherein the hydrogen donor compound is selected from the group consisting of 2,4-dimethyl-3-pentanol, 2,6-dimethyl-4-heptanol, formic acid, and mixtures thereof.

5. The method of claim 1, wherein the metal catalyst is used in an amount of 0.01 to 0.12 mole equivalent based on 1 mole equivalent of the amine compound.

6. The method of claim 1, wherein the acyl donor compound is used in an amount of 1.7 to 3 mole equivalent based on 1 mole equivalent of the amine compound.

7. The method of claim 1, wherein the biocatalyst is selected from the group consisting of a fixed Pseudomonas cepacia lipase, a fixed Candida antarctica lipase, and mixtures thereof.

8. The method of claim 1, wherein the biocatalyst is used in an amount of 15 grams to 150 grams based on 1 mole of the amine compound.

9. The method of claim 1, wherein the chiral amide compound preparation process is performed at room temperature up to 110°.

10. The method of claim 1, wherein the chiral amide compound preparation process is performed under an inert gas atmosphere, or when $R_1$ and $R_2$ are connected to form a ring selected from the group consisting of a substituted or unsubstituted $C_7$-$C_{18}$ arylalkyl, a substituted or unsubstituted $C_3$-$C_{20}$ heteroarylalkyl, a substituted or unsubstituted $C_3$-$C_{15}$ cycloalkyl, a substituted or unsubstituted $C_3$-$C_{15}$ cycloalkenyl, a substituted or unsubstituted $C_6$-$C_{15}$ cycloalkynyl, or a substituted or unsubstituted $C_3$-$C_{20}$ heterocycloalkyl, and the chiral amide compound preparation process is performed under a hydrogen atmosphere.

11. The method of claim 1, wherein the mixture is included at a concentration of 0.1 to 0.6M in an organic solvent.

12. The method of claim 1, wherein the hydrolysis process is performed using an acid solution.

* * * * *